(12) United States Patent
Komiyama et al.

(10) Patent No.: US 6,319,933 B1
(45) Date of Patent: Nov. 20, 2001

(54) AZOLE DERIVATIVES

(75) Inventors: Susumu Komiyama, Yokohama; Nobuo Shimma, Chigasaki; Takuo Tsukuda, Odawara, all of (JP)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/814,630

(22) Filed: Mar. 22, 2001

(30) Foreign Application Priority Data

Apr. 17, 2000 (EP) .................................................. 00108367
Jun. 13, 2000 (EP) .................................................. 00112488

(51) Int. Cl.[7] .................. A61K 31/4196; A61K 31/433; A61K 31/427
(52) U.S. Cl. ......................... 514/363; 514/365; 514/381; 548/262.2; 548/127; 548/128; 548/146; 546/268.7
(58) Field of Search ..................... 514/363, 381, 514/365; 548/127, 262.2, 128, 146; 546/268.7

(56) References Cited

U.S. PATENT DOCUMENTS

| | | | |
|---|---|---|---|
| 4,935,049 | * | 6/1990 | Kramer et al. ............................ 71/90 |
| 5,789,429 | * | 8/1998 | Naito et al. ............................ 518/343 |
| 5,792,781 | * | 8/1998 | Naito et al. ............................ 518/383 |
| 5,900,486 | | 9/1997 | Ichihara et al. ....................... 548/204 |
| 5,962,686 | | 1/1999 | Ichihara et al. ....................... 544/364 |

FOREIGN PATENT DOCUMENTS 667 346  8/1991 (EP) .
440 372  8/1995 (EP) .
92/17474 10/1992 (WO) .

OTHER PUBLICATIONS

Konosu et al., Chem. Pharm. Bull., vol. 39(9). 2241–2246 (1991).
Tsuruoka et al., Chem. Pharm. Bull., vol. 46, pp. 623–630 (1998).
W.D Langley, Organic Synthesis, John Wiley & Sons, Inc. NY, vol. 1, pp. 127–128 (1941).
Corrao et al., J. Org. Chem., vol. 55, pp. 4484—4487 (1990).

* cited by examiner

Primary Examiner—Floyd D. Higel
Assistant Examiner—Kamal Saeed
(74) Attorney, Agent, or Firm—George W. Johnston; Dennis P. Tramaloni

(57) ABSTRACT

The present invention is directed to new 1-(1H-1,2,4-triazol-1-yl)butan-2-ol derivatives of the formula (I),

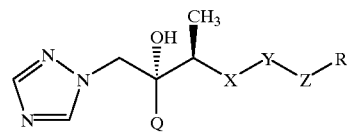

(I)

and pharmaceutically acceptable salts thereof wherein Q, R, X, Y and Z are the same as defined in the claims and the description. 1-(1H-1,2,4-triazol-1-yl)butan-2-ol derivatives of the present invention have antifungal activity and are useful for the treatment of fungal diseases.

15 Claims, No Drawings

AZOLE DERIVATIVES

BACKGROUND OF THE INVENTION

Azole antifungal agents are currently most frequently used for systemic mycosis, but none of them fully fulfil the necessary clinical requirement; such as efficacy against major systemic mycoses including disseminated aspergillosis, safety, and water solubility for parenteral formulation. Although the systematic mycoses caused by Candida, Cryptococcus and Aspergillus spp. are still major infections, there is an increasing medical need for new antifungal agents with broader spectrum that cover not only the above mentioned major pathogens but also emerging pathogens such as mucor spp. Several new azole type agents have been developed to fulfil these unmet medical needs, such as the compounds disclosed in EP 0 667 346 and EP 0 440 372. The present invention intends to provide antifungal agents having broad antifungal spectrum covering Aspergillus as well as mucor spp., their intermediates, a process for their manufacture, an antifungal composition containing them and the use thereof.

SUMMARY OF THE INVENTION

The present invention provides compounds of the general formula

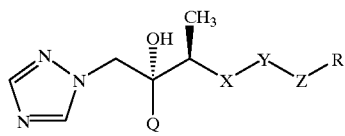

which possess a broad spectrum of antifungal activity. The compounds of the present invention have a surprisingly high level of antifungal activity, in particular against Aspergillus spp., and mucor spp. such as Rhizopus spp., and Absidia spp.

DETAILED DESCRIPTION OF THE INVENTION

The present invention relates to novel 1-(1H-1,2,4-triazol-1-yl)butan-2-ol derivatives of the formula (I),

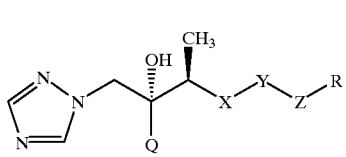

(I)

wherein
- Q is a phenyl ring, optionally substituted by 1 to 3 halogen atom(s);
- R is hydrogen, hydroxy, carboxy, carbamoyl, cyano, lower-alkyl, lower-alkoxycarbonyl or lower-alkoxy, whereas lower-alkyl, lower-alkoxycarbonyl and lower-alkoxy may be substituted by one or more halogen, lower-alkyl, di-lower-alkylamino or lower-alkoxy;
- X is a 5 or 6 membered hetero-aromatic ring;
- Y is phenyl or pyridyl, each of which may be substituted by one or more halogen, cyano, lower-alkyl, di-lower-alkylamino, lower-alkyloxy, acyl, lower-alkoxycarbonyl;
- Z is a sulfur and nitrogen containing 5 membered hetero-aromatic ring; and pharmaceutically acceptable salts thereof.

As used above, the following terms have the meanings indicated:

The term "lower" is used to mean a radical consisting of 1 to 5, preferably 1 to 4 carbon atom(s), unless otherwise indicated.

The term "alkyl" refers to a branched or straight chain monovalent saturated aliphatic hydrocarbon radical of one to twenty carbon atoms, preferably of one to sixteen carbon atom(s).

The term "lower alkyl" refers to a branched or straight chain monovalent alkyl radical of one to six carbon atom(s), preferably one to four carbon atom(s). This term is further exemplified by such radicals as methyl, ethyl, n-propyl, isopropyl, n-butyl, i-butyl, tert-butyl and the like.

The term "halogen atom" refers to fluorine, chlorine, bromine and iodine.

The term "heteroatom" refers to N, O and S.

The term "acyl" refers to the group —C(O)—R', where R' is a lower alkyl.

The term "lower alkoxycarbonyl" refers to the group —C(O)OR', where R' is a lower alkyl.

The term "lower alkoxy" refers to the group —O—R', where R' is a lower alkyl.

The term "di-lower alkylamino" refers to two independently selected lower alkyl groups attached to a nitrogen atom, i.e., —N(-lower alkyl)-lower alkyl.

The present invention also relates to pharmaceutical compositions containing above 1-(1H-1,2,4-triazol-1-yl)butan-2-ol derivatives, the use of such derivatives for the prophylaxis or treatment of mycoses as well as to processes for production of such 1-(1H-1,2,4-triazol-1-yl)butan-2-ol derivatives.

Preferable embodiments of the groups for formula I are as follows:

In the definition Z, the term "sulfur and nitrogen containing 5 membered hetero-aromatic ring" preferably means a group selected from the group consisting of the groups represented by the formula,

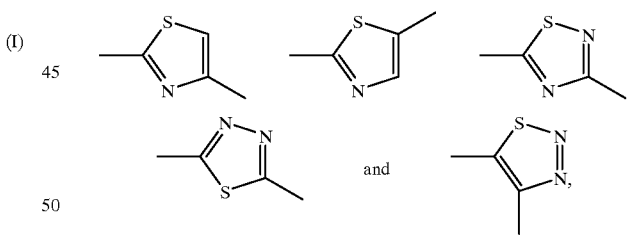

more preferably

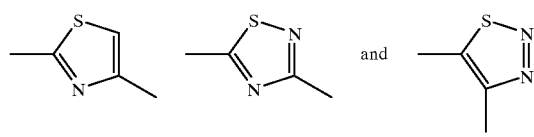

viz. thiazol-2,4-diyl, 1,2,4-thiadiazol-3,5-diyl and 1,2,3-thiadiazol-4,5-diyl.

In the definition X, the term "5 or 6 membered hetero-aromatic ring" preferably means a group selected from the group consisting of the groups represented by the formula:

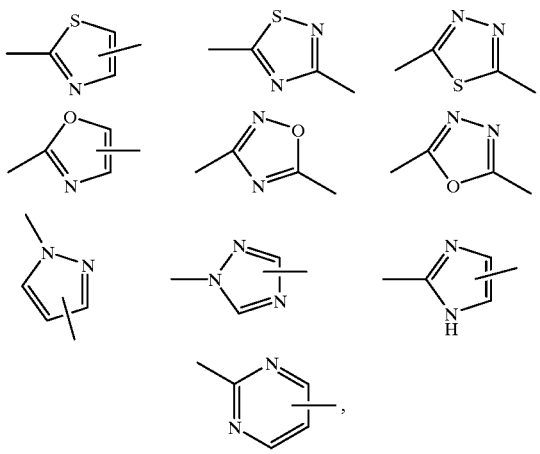

more preferably

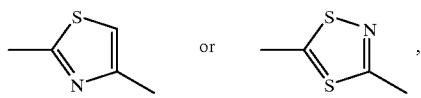

viz. thiazol-2,4-diyl and 1,2,4-thiadiazol-3,5-diyl.

In the definition Y, tie term "phenyl or pyridyl which may be substituted by one or more halogen, cyano, lower-alkyl, di-lower-alkylamino, lower-alkyloxy, acyl, lower-alkoxycarbonyl" preferably means o-phenylene, m-phenylene, p-phenylene, pyridin-2,4-diyl, pyridin-2,5-diyl, pyridin-2,6-diyl and the like. More preferably, Y is m-phenylene, p-phenylene or pyridin-2,5-diyl. The most preferable Y is p-phenylene.

Preferable residues R in accordance with the present invention are hydrogen, hydroxy, lower-alkyl, e.g. methyl or ethyl, lower-alkoxycarbonyl, e.g. ethoxy-carbonyl, and lower-alkyl substituted by one or more halogen, preferably fluoro, e.g. trifluoromethyl or pentafluoroethyl.

The preferable embodiments of —Z—R in the formula (I) are thiazole-2-yl, 4-methyl-thiazol-2-yl, 4-isopropyl-thiazol-2-yl, 4-ethyl-thiazol-2-yl, 4-trifluoromethyl-thiazol-2-yl, 4-pentafluoroethyl-thiazol-2-yl, 4-acetyl-thiazol-2-yl, 4-carboxy-thiazol-2-yl, 4-cyano-thiazol-2-yl, 4-methoxy-thiazol-2-yl, 4-ethoxycarbonyl-thiazol-2-yl, 4-chloro-thiazol-2-yl, 4-hydroxy-thiazol-2-yl, 1,2,4-thiadiazol-3-yl, 5-methyl-1,2,4-thiadiazol-3-yl, 5-ethyl-1,2,4-thiadiazol-3-yl, 5-isopropyl-1,2,4-thiadiazol-3-yl, 5-trifluoromethyl-1,2,4-thiadiazol-3-yl, 5-pentafluoroethyl-1,2,4-thiadiazol-3-yl, 5-acetyl-1,2,4-thiadiazol-3-yl, 5-carboxy-1,2,4-thiadiazol-3-yl, 5-cyano-1,2,4-thiadiazol-3-yl, 5-methoxy-1,2,4-thiadiazol-3-yl, 5-ethoxycarbonyl-1,2,4-thiadiazol-3-yl, 5-chloro-1,2,4-thiadiazol-3-yl, 1,3,4-thiadiazol-5-yl, 2-methyl-1,3,4-thiadiazol-5-yl, 2-ethyl-1,3,4-thiadiazol-5-yl, 2-isopropyl-1,3,4-thiadiazol-5-yl, 2-trifluoromethyl-1,3,4-thiadiazol-5-yl, 2-pentafluoroethyl-1,3,4-thiadiazol-5-yl, 2-acetyl-1,3,4-thiadiazol-5-yl, 2-carboxy-1,3,4-thiadiazol-5-yl, 2-cyano-1,3,4-thiadiazol-5-yl, 2-methoxy-1,3,4-thiadiazol-5-yl, 2-ethoxycarbonyl-1,3,4-thiadiazol-5-yl, 2-chloro-1,3,4-thiadiazol-5-yl, 1,2,3-thiadiazol-4-yl, 5-methyl-1,2,3-thiadiazol-4-yl, 5-ethyl-1,2,3-thiadiazol-4-yl, 5-isopropyl-1,2,3-thiadiazol-4-yl, 5-trifluoromethyl-1,2,3-thiadiazol-4-yl, 5-pentafluoroethyl-1,2,3-thiadiazol-4-yl, 5-acetyl-1,2,3-thiadiazol-4-yl, 5-carboxy-1,2,3-thiadiazol-4-yl, 5-cyano-1,2,3-thiadiazol-4-yl, 5-methoxy-1,2,3-thiadiazol-4-yl, 5-ethoxycarbonyl-1,2,3-thiadiazol-4-yl, 5-chloro-1,2,3-thiadiazol-4-yl and the like, more preferably, thiazole-2-yl, 4-methyl-thiazol-2-yl, 4-ethyl-thiazol-2-yl, 4-trifluoromethyl-thiazol-2-yl, 4-pentafluoroethyl-thiazol-2-yl, 4-ethoxycarbonyl-thiazol-2-yl, 4-chloro-thiazol-2-yl, 4-hydroxy-thiazol-2-yl, 1,2,4-thiadiazol-3-yl, 5-methyl-1,2,4-thiadiazol-3-yl, 5-ethyl-1,2,4-thiadiazol-3-yl. The most preferable residues —Z—R are 1,2,3-thiadiazol-4-yl and thiazole-2-yl.

In the definition of Q, the term "phenyl ring optionally substituted by 1 to 3 halogen atom(s)" preferably means 2-fluorophenyl, 4-fluorophenyl, 2-chlorophenyl, 4-chlorophenyl, 2-bromophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, 4-bromo-2,5-difluorophenyl and the like; more preferably 2-fluorophenyl, 4-fluorophenyl, 2,4-difluorophenyl, 2,5-difluorophenyl, 2,4,6-trifluorophenyl, 4-bromo-2,5-difluorophenyl. The most preferable residues Q are 2,4-difluorophenyl and 2,5-difluorophenyl.

In a preferred embodiment, the present invention relates to 1-(1H-1,2,4-triazol-1-yl)butan-2-ol derivatives of the above formula (I) wherein Q is a radical selected from the group consisting of 2,4-difluorophenyl and 2,5-difluorophenyl; X is a radical selected from the group consisting of 1,2,4-thiadiazol-3,5-diyl and thiazol-2,4-diyl; Y is p-phenylene; Q is 2,4-difluorophenyl or 2,5-difluorophenyl; and —Z—R is a radical selected from the group consisting of 1,2,3-thiadiazol-4-yl and thiazole-2-yl.

Preferred 1-(1H-1,2,4-triazol-1-yl)butan-2-ol derivatives in accordance with the present invention are as follows:

(2R,3R)-2-(2,4-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,5-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,4-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,5-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,4-difluorophenyl)-3-{14-[4-(thiazol-2-yl)phenyl]thiazol-2-yl}(1H-1,2,4-triazol-1-yl)butan-2-ol, (2R,3R)-2-(2,4-difluorophenyl)-3-{14-[4-(4-methylthiazol-2-yl)phenyl]thiazol-2-yl}-1-(1H-1,2,4-triazol-1-yl)butan-2-ol, (2R,3R) -2-(2,4-difluorophenyl)-3-{4-[4-(4-ethylthiazol-2-yl)phenyl]thiazol-yl}-1-(1H-1,2,4-triazol-1-yl)butan-2-ol, (2R,3R)-2-(2,4-difluorophenyl)-1-(1H-1,2,4-triazole-1-yl)-3-{4-[4-(4-trifluoromethylthiazol-2-yl)phenyl]thiazol-2-yl}butan-2-ol, 2-(4-{2-[(1R,2R)-2-(2,4-difluorophenyl)-2-hydroxy-1-methyl-3-(1H-1,2,4-triazol-1-yl)propyl]thiazol-4-yl}phenyl)thiazole-4-carboxylic acid ethyl ester, (2R,3R)-2-(2,4-difluorophenyl)-3-{3-[4-(4-methylthiazol-2-yl)phenyl]-1,2,4-thiadiazol-5-yl}-1-(1H-1,2,4-triazol-1-yl)butan-2-ol, (2R,3R)-2-(2,4-difluorophenyl)-3-{3-[4-(4-ethylthiazol-2-yl)phenyl]-1,2,4-thiadiazol-5-yl}-1-(1H-1,2,4-triazol-1-yl)butan-2-ol, (2R,3R)-2-(2,4-difluorophenyl)-1-(1H-1,2,4-triazol-1-yl)-3-{3-[4-(4-trifluoromethylthiazol-2-yl)phenyl]-1,2,4-thiadiazol-5-yl}butan-2-ol, 2-(4-{5-[(1R,2R)-2-(2,4-difluorophenyl)-2-hydroxy-1-methyl-3-(1H-1,2,4-triazol-1-yl)propyl]-1,2,4-thiadiazol-3-yl}phenyl)thiazole-4-carboxylic acid ethyl ester, (2R,3R)-2-(2,4-difluorophenyl)-3-{4-[4-(4-pentafluoroethylthiazol-2-yl)phenyl]thiazol-2-yl}-1-(1H-1,2,4-triazol-1-yl)butan-2-ol, (2R,3R)-2-(2,4-difluorophenyl)-3-{3-[4-(4-pentafluoroethylthiazol-2-yl)phenyl]-1,2,4-thiadiazol-5-yl}-1-(1H-1,2,4-triazol-1-yl)butan-2-ol, (2R,3R)-2-(2,4-difluorophenyl)-3-{4-[4-(4-hydroxythiazol-2-yl)phenyl]thiazol-2-yl}-1-(1H-1,2,4-triazol-1-yl)butan-2-ol, (2R,3R)-2-(2,4-difluorophenyl)-3-(3-{4-[5-methyl-(1,2,4-thiadiazol-3-yl)]phenyl}-1,2,4-thiadiazol-5-yl)-1-(1H-1,2,4-triazol-1-yl)butan-2-ol, (2R,3R)-2-(2,4-difluorophenyl)-3-(4-{4-[5-methyl-(1,2,4-thiadiazol-3-yl)]phenyl}thiazol-2-yl)-1-(1H-1,2,4-triazol-1-yl)butan-2-ol, (2R,3R)-2-(2,4-difluorophenyl)-3-(4-{4-[5-ethyl-(1,2,4-thiadiazol-3-yl)]phenyl}thiazol-2-yl)-1-(1H-1,2,4-triazol-1-yl)butan-2-ol, (2R,3R)-2-(2,4-difluorophenyl)-3-(3-{4-[5-ethyl-(1,2,4-thiaziazol-3-yl)]phenyl}-1,2,4-thiadiazol-5-yl)-1-(1H-1,2,4-triazol-1-yl)butan-2-ol, and the like.

Particularly preferred 1-(1H-1,2,4-triazol-1-yl)butan-2-ol derivatives in accordance with the present invention are as follows:

(2R,3R)-2-(2,4-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,5-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,4-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,5-difluorophenyl)-3-{4-[4-(1,2,3-thiadiazol-4-yl)phenyl thiazol-2-yl}-1-(1H-1,2,4-triazol-1-yl)butan-2-ol, (2R,3R)-2-(2,4-difluorophenyl)-3-{4-[4-(thiazole-2-yl)phenyl]thiazol-2-yl}-1-(1H-1,2,4-triazol-1-yl)butan-2-ol, (2R,3R)-2-(2,4-difluorophenyl)-3-{4-[4-(4-methylthiazol-2-yl)phenyl]thiazol-1-yl}-1-(1H-1,2,4-triazol-1-yl)butan-2-ol, (2R,3R)-2-(2,4-difluorophenyl)-3-{4-[4-(4-ethylthiazol-2-yl)phenyl]thiazol-1-yl}-1-(1H-1,2,4-triazol-1-yl)butan-2-ol, (2R,3R)-2-(2,4-difluorophenyl)-1-(1H-1,2,4-triazole-1-yl)-3-{4-[4-(4-trifluoromethyl-thiazol-2-yl)phenyl]thiazol-2-yl}butan-2-ol, 2-(4-{2-[(1R,2R)-2-(2,4-difluorophenyl)-2-hydroxy-1-methyl-3-(1H-1,2,4-triazol-1-yl)propyl]thiazol-4-yl}phenyl)thiazole-4-carboxylic acid ethyl ester, (2R,3R)-2-(2,4-difluorophenyl)-3-(4-{4-[5-methyl-(1,2,4-thiadiazol-3-yl)]phenyl}thiazol-2-yl)-1-(1H-1,2,4-triazol-1-yl)butan-2-ol, and (2R,3R)-2-(2,4-difluorophenyl)-3-(4-{4-[5-ethyl-(1,2,4-thiadiazol-3-yl)]phenyl}thiazol-2-yl)-1-(1H-1,2,4-triazol-1-yl)butan-2-ol.

The novel 1-(1H-1,2,4-triazol-1-yl)butan-2-ol derivatives of the formula (I) can be produced by one or more of the following methods:

Process A

The desired 1-(1H-1,2,4-triazol-1-yl)butan-2-ol derivatives of the formula (I) in which X is a thiazole can be produced by condensation of a compound represented by the formula (II) wherein Q is the same as defined above with an α-bromoketone of the formula (III):

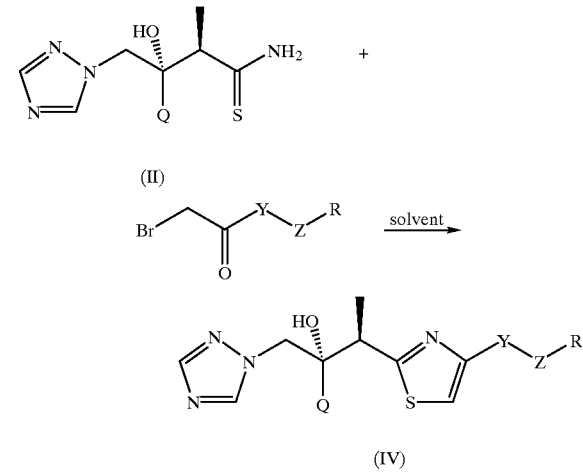

wherein Q, R, Y and Z are the same as defined above.

Specific examples of the compound of the formula (IV) may include, for example, the following compounds: (2R,3R)-2-(2,4-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,5-difluorophenyl)-3-{4-[4-(1,2,3-thiadiazol-4-yl)phenyl]thiazol-2-yl}-1-(1H-1,2,4-triazol-1-yl)butan-2-ol and the like.

This reaction proceeds in a solvent such as chloroform, dichloromethan, acetonitrile, dimethylformamide, methanol, ethanol, and the like, and at temperature between 0° C. and 100° C. for between 1 to 12 hours, preferably at 20° C. to 60° C.

Process B

The desired 1-(1H-1,2,4-triazol-1-yl)butan-2-ol derivatives of the formula (I) in which X, Y and Q are the same as defined above and —Z—R is thiazol-2-yl can be produced by condensation of a compound represented by the formula (V) wherein Q is the same as defined above with an a-bromoketone represented by the formula (VI):

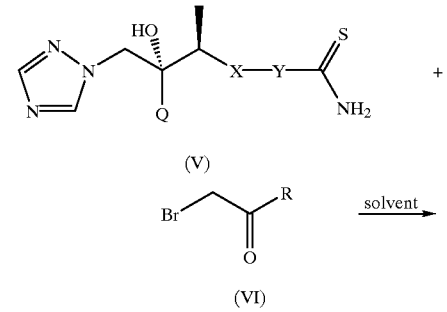

(VII)

wherein R is the same as defined above.

Specific examples of the compound represented by the formula (VII) may include, for example, the following compounds: (2R,3R)-2-(2,4-difluorophenyl)-3-{4-[4-(thiazol-2-yl)phenyl]thiazol-2-yl}-1-(1H-1,2,4-triazol-1-yl)butan-2-ol, (2R,3R)-2-(2,4-difluoro-phenyl)-3-{4-[4-(4-methylthiazol-2-yl)phenyl]thiazol-2-yl}-1-(1H-1,2,4-triazol-1-yl)butan-2-ol, (2R,3R)-2-(2,4-difluorophenyl)-3-{4-[4-(4-ethylthiazol-2-yl)phenyl]thiazol-2-yl}-1-(1H-1,2,4-triazol-1-yl)butan-2-ol, (2R,3R)-2-(2,4-difluorophenyl)-1-(1H-1,2,4-triazol-1-yl)-3-{4-[4-(4-ethylthiazol-2-yl)phenyl]thiazol-2-yl}butan-2-ol, 2-(4-{2-(1R,2R)-2-(2,4-difluorophenyl)-2-hydroxy-1-methyl-3-(1H-1,2,4-triazol-1-yl)propyl]-thiazol-4-yl}phenyl)thiazole-4-carboxylic acid ethyl ester, (2R,3R)-2-(2,4-difluorophenyl)-3-{4-[4-(4-pentafluoroethylthiazol-2-yl)phenyl]thiazol-2-yl}-1-(1H-1,2,4-triazol-1-yl)butan-2-ol, (2R,3R)-2-(2,4-difluorophenyl)-3-{4-[4-(4-hydroxythiazol-2-yl)phenyl]thiazol-2-yl}-1-(1H-1,2,4-triazol-1-yl)butan-2-ol and the like.

This reaction proceeds in a solvent such as chloroform, dichloromethan, acetonitrile, dimethylformamide, methanol, ethanol, and the like, and at temperature between 0° C. and 100° C. for between 1 to 12 hours, preferably at 20° C. to 60° C.

Compound (VII) where R is hydrogen can also be produced by condensation of a compound V, where X, Y and Q are as above, with chloroacetal, the reaction conditions being about as described in Example 5.

Process C

The desired 1-(1H-1,2,4-triazol-1-yl)butan-2-ol derivatives of the formula (I) in which X and Y are the same as defined above and —Z—R is 1,2,4-thiadiazol-3-yl can be produced by condensation between a compound represented by the formula (V) wherein Q is the same as defined above and thioamide represented by the formula (VIII):

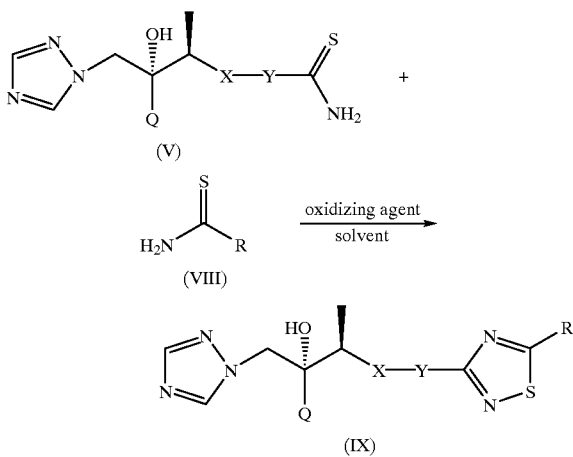

wherein R is the same as defined above.

Specific examples of the compound represented by the formula (IX) may include, for example, the following compounds: (2R,3R)-2-(2,4-difluorophenyl)-3-(3-{4-[5-methyl-(1,2,4-thiaziazol-3-yl)]phenyl}-1,2,4-thiadiazol-5-yl)-1-(1H-1,2,4-triazol-1-yl)-butan-2-ol, (2R,3R)-2-(2,4-difluorophenyl)-3-(4-{4-[5-methyl-(1,2,4-thiadiazol-3-yl)]phenyl}thiazol-2-yl)-1-(1H-1,2,4-triazol-1-yl)butan-2-ol, (2R,3R)-2-(2,4-difluorophenyl)-3-(4-{4-[5-ethyl-(1,2,4-thiadiazol-3-yl)]phenyl}thiazol-2-yl)-1-(1H-1,2,4-triazol-1-yl)butan-2-ol, (2R,3R)-2-(2,4-difluorophenyl)-3-{3-[4-[5-ethyl-(1,2,4-thiaziazol-3-yl)]phenyl]-1,2,4-thiadiazol-5-yl}-1-(1H-1,2,4-triazol-1-yl) butan-2-ol and the like.

This reaction proceeds in a solvent such as chloroform, dichloromethane, acetonitrile, dimethylformamide, methanol, ethanol, tetrahydrofurane and the like in the presence of oxidizing reagent such as iodine, selenium dioxide, n-butyl nitrite and the like, and at temperature between 25° C. and 100° C. for between 5 to 48 hours, preferably at 20° C. to 50° C.

Process D

The desired 1-(1H-1,2,4-triazol-1-yl)butan-2-ol derivatives of the formula (I) in which X is a 1,2,4-thiadiazole can be produced by condensation of a compound represented by the formula (II) with a thioamide represented by the formula (X):

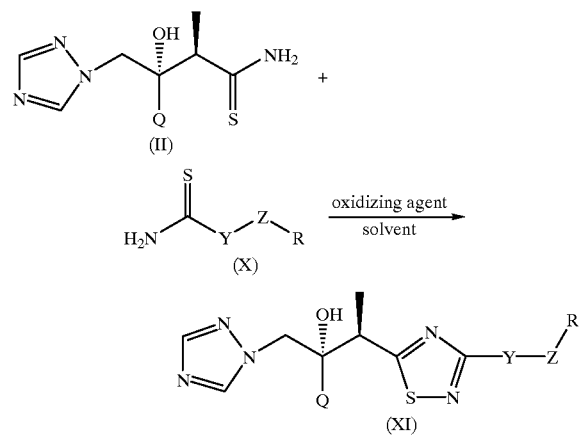

wherein Q, R, Y and Z are the same as defined above.

Specific examples of the compound represented by the general formula (XI) may include, for example, the following compounds: (2R,3R)-2-(2,4-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,5-difluorophenyl)-3-{3-[4-(1,2,3-thiadiazol-4-yl) phenyl]-1,2,4-thiadiazol-5-yl}-1-(1H-1,2,4-triazol-1-yl)butan-2-ol, (2R,3R)-2-(2,4-difluorophenyl)-3-{3-[4-(4-methylthiazol-2-yl)phenyl]-1,2,4-thiadiazol-5-yl}-1-(1H-1,2,4-triazol-1-yl)butan-2-ol, (2R,3R)-2-(2,4-difluorophenyl)-3-{3-{4-(4-ethylthiaol-2-yl)phenyl]-1,2,4-thiadiazol-5-yl}-1-(1H-1,2,4-triazol-1-yl)butan-2-ol, (2R,3R)-2-(2,4-difluorophenyl)-1-(1H-1,2,4-triazol-1-yl)-3-{3-[4-(4-trifluoromethylthiazol-2-yl)phenyl]-1,2,4-thiadiazol-5-yl}butan-2-ol, 2-(4-15-[(1R,2R)-2-(2,4-difluorophenyl)-2-hydroxy-1-methyl-3-(1H-1,2,4-triazol-1-yl)propyl]-1,2,4-thiadiazol-3-yl}phenyl) thiazole-4-carboxylic acid ethyl ester, (2R,3R)-2-(2,4-difluorophenyl)-3-{3-[4-(4-pentafluoroethylthiazol-2-yl)phenyl]-1,2,4-thiadiazol-5-yl}-1-(1H-1,2,4-triazol-1-yl)butan-2-ol and the like.

This reaction proceeds in a solvent such as chloroform, dichloromethane, acetonitrile, dimethylformamide, methanol, ethanol, tetrahydrofurane and the like in the presence of oxidizing reagent such as iodine, selenium dioxide, n-butyl nitrite and the like, and at temperature between 25° C. and 100° C. for between 5 to 48 hours, preferably at 20° C. to 50° C.

Process E

The desired 1-(1H-1,2,4-triazol-1-yl)butan-2-ol derivatives of the formula (I) in which X is a 1,2,4-oxadiazole can be produced by condensation of a compound represented by the formula (XII) with an acid chloride represented by the formula (XIII) in a manner similar to that described in *J. Het. Chem.* 26, 125 (1989):

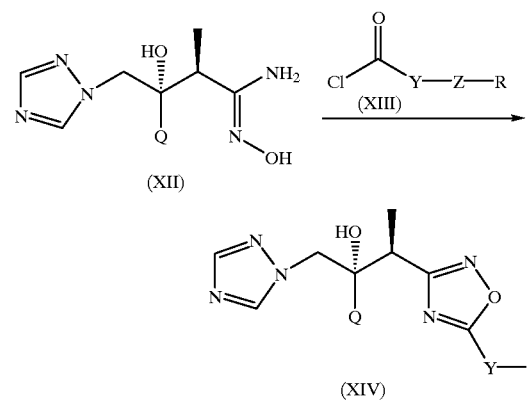

wherein Q, R, Y and Z are the same as defined above.

This reaction proceeds in a solvent such as pyridine, pyrazine, quinoline and the like at temperatures between 25° C. and 100° C. for 5 to 48 hours, preferably at 50° C. to 80° C.

Process F

The desired 1-(1H-1,2,4-triazol-1-yl)butan-2-ol derivatives of the formula (I) in which X is a 1,3,4-oxadiazole can be produced by condensation of a compound represented by the formula (XV) with an acid chloride represented by the formula (XIII) in a manner similar to that described in *Chem. Ber.*, 1555 (1961):

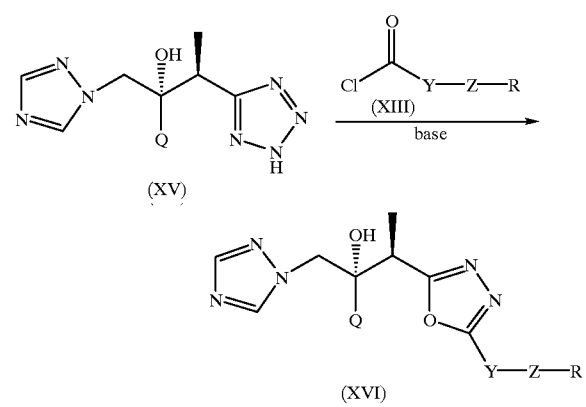

wherein Q, R, Y and Z are the same as defined above.

This reaction proceeds in a solvent such as pyridine, pyrazine, quinoline and the like at temperatures between 25° C. and 100° C. for 5 to 48 hours, preferably at 50° C. to 80° C.

Process G

The desired 1-(1H-1,2,4-triazol-1-yl)butan-2-ol derivatives of the formula (I) in which X is a pyrimidine can be produced by condensation of a compound represented by the formula (XVII) with an a-ketoaldehyde represented by the formula (XVIII) or with a dialdehyde represented by the formula (XIX) in a manner similar to that described in *J. Het. Chem.* 51(1974):

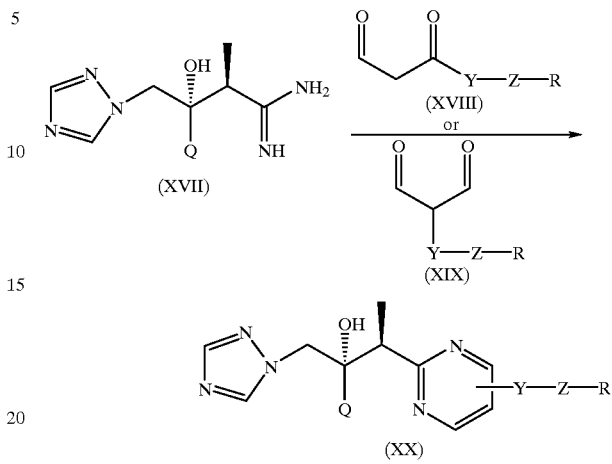

wherein Q, R, Y and Z are the same as defined above.

This reaction proceeds in a solvent such as methanol, ethanol, propanol, butanol and the like at temperature between 25° C. and 100° C. for between 5 to 48 hours, preferably at 50° C. to 80° C.

Process H

The desired 1-(1H-1,2,4-triazol-1-yl)butan-2-ol derivatives of the formula (I) in which X is a pyrazole can be produced by condensation of a compound represented by the formula (XXI) with an a-ketoaldehyde represented by the formula (XVIII) or a dialdehyde represented by the formula (XIX) in a manner similar to that described in *J. Het. Chem.* 51(1974):

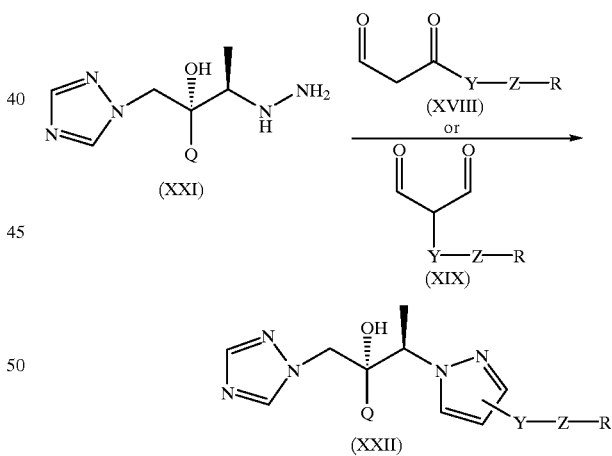

wherein Q, R, Y and Z are the same as defined above.

This reaction proceeds in a solvent such as methanol, ethanol, propanol, butanol and the like at temperature between 25° C. and 100° C. for 5 to 48 hours, preferably at 50° C. to 80° C.

Other desired 1-(1H-1,2,4-triazol-1-yl)butan-2-ol derivatives of the formula (I) in which X is as defined above can be produced by similar condensation reactions as described in the above processes, using appropriate nucleophiles and electrophiles.

Synthesis of Starting Material

The starting compounds (II), (XXIII) and (XXIV) can be prepared by using known methods (Konotsu T. et al, *Chem.*

Pharm. Bull., 39, 2241–2246(1991)). The starting compounds (III) and (VI) can be prepared by using known methods (Langley, W. O., Organic Synthesis, 1, 127 (1941)). The starting compound (V) can be prepared by using known methods (Tsuruoka A. et al, Chem. Pharm. Bull., 46, 623–630 (1998)). The starting compound (VIII) and (X) can be prepared by using known methods (Corrao, S. L. et al., J. Org. Chem., 55,4486–4487 (1990)). The starting compounds (XII), (XVII), (XXI) and (XV) can be prepared by using known methods (WO92/17474).

caused by, for example, Candida, Cryptococcus, Aspergillus, Paracoccidiodes, Sporotric, Exophiala, Blastomyces or Histoplasma, especially against Aspergillus spp., Rhizopus spp., and Absidia spp.

Determination of in vitro Antifungal Activity

In vitro antifungal activities of 1-(1H-1,2,4-triazol-1-yl)butan-2-ol derivatives of the formula (I) of the present invention were evaluated by determining the 80% inhibitory concentration ($IC_{80}$), which was calculated as the lowest concentration of an antifungal to inhibit the growth of

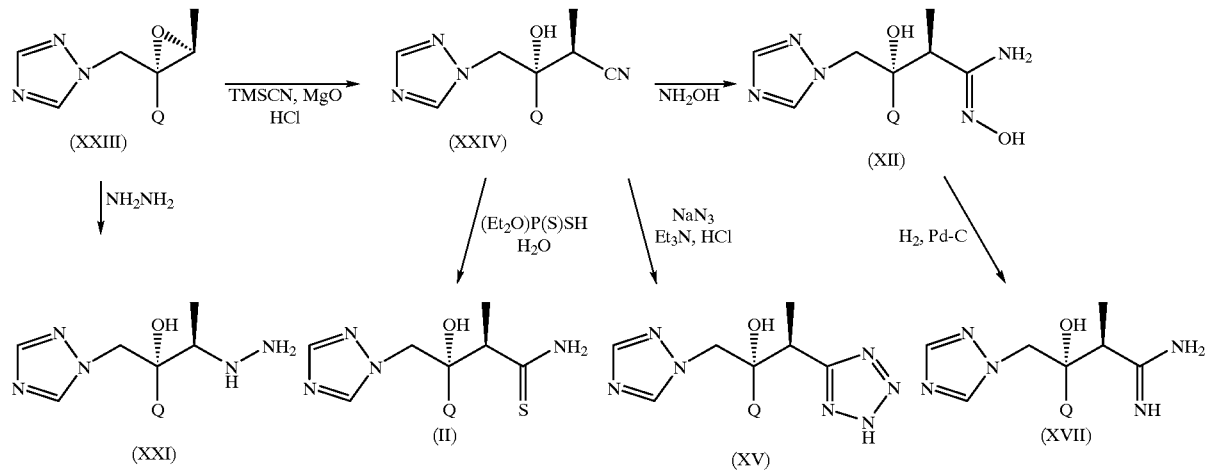

TMSCN=trimethylsilyl cyanide.

The manufacture of the pharmaceutically acceptable acid addition salts of 1-(1H-1,2,4-triazol-1-yl)butan-2-ol derivatives of the formula (I) can be carried out by treating a free base of the compound represented by the formula (I) with an acid using a conventional procedure for the salt formation. Examples of therapeutically acceptable acids useful in the above process are inorganic acids (e.g. hydrochloric acid, hydrobromic acid, phosphoric acid, nitric acid, sulfuric acid) and organic acids (e. g. oxalic acid, acetic acid, formic acid, trifluoroacetic acid, maleic acid, succinic acid, fumaric acid, tartaric acid, citric acid, salicylic acid, sorbic acid, lactic acid, methanesulfonic acid). Moreover, the compounds of the formula (I) can be converted into hydrates or solvates and their salts by various methods known to those skilled in the art. 1-(1H-1,2,4-Triazol-1-yl)butan-2-ol derivatives of the formula (I) and pharmaceutically acceptable salts thereof are very active antimycotic agents.

They are active against a variety of fungal species, including Candida albicans, Cryptococcus neoformans, Aspergillus fumigatus, Trichophyton spp., Microsporum spp., Exophiala spp., Rhizopus spp., Absidia spp., Blastomyces dermatitidis, and Histoplasma capsulatum.

Thus, 1-(1H-1,2,4-triazol-1-yl)butan-2-ol derivatives of the formula (I) of the present invention are useful for topical and systemic treatment of mycoses in animals as well as in human. Accordingly, the present invention comprises the use of the above compounds for the manufacture of medicaments for the prophylaxis and treatment of mycoses and the corresponding pharmaceutical compositions which comprise 1-(1H-1,2,4-triazol-1-yl)butan-2-ol derivatives of the formula (I) as defined above and a pharmaceutically acceptable carrier.

For example, they are useful in treating topical and mucous Trichophyton or Microsporum species. They may also be used in the treatment of systemic fungal infections fungus to 20% turbidity compared with the drug-free control growth spectrophotometrically. The $IC_{80}$ values were determined by the broth micro-dilution procedure based on NCCLS Approved Standard with the following minor modifications:

Document M27-A

National Committee for Clinical Laboratory Standards. (1997) Reference method for broth dilution antifungal susceptibility testing for yeasts. Approved standard.

Modifications

Yeast Nitrogen Base (YNB; Difco Lab.) supplemented with 1% glucose and 0.25% $K_2HPO_4$ was used as testing medium for yeast, the same medium solidified with 0.2% low melting point agarose (BRL) was used for filamentous fungi. Inoculum size was $1-3\times10^4$ cells/ml, and incubation was performed for 1–2 days at 35° C.

The inhibitory activity of 1-(1H-1,2,4-triazol-1-yl)butan-2-ol derivatives of the formula (I) against in vitro growth of Candida albicans, Aspergillus fumigatus, Rhizopus oryzea, and Absidia corymbifera is summarized in Table 1comparing with 2-(2,4-difluorophenyl)-1,3-bis(1H-1,2,4-triazol-1-ylmethyl)propan-2-ol (Fluconazole; Pfizer).

TABLE 1

[0057] In vitro antifungal activity ($IC_{80}$; μg/ml)

| Example | C. albicans (CY1002) | A. fumigatus (437) | R. oryzea (CFF1118) | A. cormybifera (CF1001) |
|---|---|---|---|---|
| 1 | 0.00093 | 0.11 | 0.0023 | 0.0057 |
| 2 | 0.0014 | 0.036 | 0.011 | 0.047 |
| 3 | 0.011 | 0.14 | 0.0029 | 0.024 |
| 4 | 0.011 | 0.17 | 0.0028 | 0.017 |
| 5 | 0.0059 | 0.35 | 0.0047 | 0.3 |
| 6 | 0.021 | 0.67 | 0.095 | 0.33 |

TABLE 1-continued

[0057] In vitro antifungal activity (IC$_{80}$; μg/ml)

| Example | C. albicans (CY1002) | A. fumigatus (437) | R. oryzea (CFF1118) | A. cormybifera (CF1001) |
|---|---|---|---|---|
| 7 | 0.024 | 0.39 | 0.069 | 0.34 |
| 9 | 0.022 | 0.5 | 0.036 | 0.17 |
| 18 | 0.0031 | 0.28 | 0.046 | 0.19 |
| 19 | 0.016 | 0.3 | 0.044 | 0.25 |
| Fluconazole | 0.91 | >200 | >200 | >200 |

For clinical use, 1-(1H-1,2,4-triazol-1-yl)butan-2-ol derivatives of the formula (I) or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

In more detail, as mentioned earlier, medicaments containing a compound of formula I are also an object of the present invention, as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, table, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The antifungal can also be administered in the form of a suppository or pessary, or they may be applied topically in the form of a lotion, solution, cream, ointment or dusting powder.

The daily dosage level of 1-(1H-1,2,4-triazol-1-yl)butan-2-ol derivatives of the formula (I) of the present invention is from 0.1 to 100 mg/kg when administered by either the oral or parenteral route. Thus tablets or capsules can contain from 5 mg to 1000 mg of active compound for administration singly or two or more at a time as appropriate. In any event the actual dosage can be weight and response of the particular patient.

1-(1H-1,2,4-Triazol-1-yl)butan-2-ol derivatives of the formula (I) of the present invention and salts thereof have activity against a variety of plant pathogenic fungi, including for example Pyricularia oryzae, Pythium aphanidermatum, Alternaria spp., and Paecilomyces variotii.

Thus, they can be applied for agricultural and horticultural purposes preferably in the form of a composition formulated as dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compounds having herbicidal or insecticidal activity or additional antifungal compositions can be applied in a number of ways, for example they can be applied directly to the plant foliage, stems, branches, seeds or roots or to the soil or other growing medium, and they may be used not only to eradicate disease, but also prophylactically to protect the plants or seeds from fungal attack.

The following examples illustrate the preferred methods for the preparation of the compounds of the present invention, which are not intended to limit the scope of the invention thereto.

EXAMPLE 1

(2R,3R)-2-(2,4-Difluorophenyl)-3-{3-[4-(1,2,3-thiadiazol-4-yl)phenyl]-1,2,4-thiadiazol-5-yl}-1-(1H-1,2,4-triazol-1-yl)butan-2-ol.

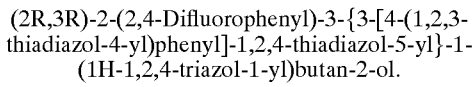

To a mixture of (2R,3R)-3-(2,4-difluorophenyl)-3-hydroxy-2-methyl-4-(1H-1,2,4-triazol-1-yl)thiobutyramide (62.2 mg) and 4-(1,2,3-thiadiazol-4-yl)phenylthioamide (132.2 mg) in ethanol (3.0 ml) was added iodine (303.8 mg) at room temperature. The solution was stirred for 60 hours and diluted with ethyl acetate (10 ml), washed with 0.1mol/l sodium thiosulfate solution (10 ml) and brine (10 ml), dried over anhydrous sodium sulfate, then concentrated in vacuo. The mixture was purified by silica gel column chromatography developed by hexane-ethyl acetate (1:1) to give (2R, 3R)-2-(2,4-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol as pale yellow solid (21.1 mg). EI-MS: m/z 498 (M$^+$); $^1$H-NMR (DMSO-d6): δ 1.19(3H, d, J=6.9 Hz), 4.31(1H, q, J=7 Hz), 4.54(1H, d, J=14.5 Hz), 4.80(1H, d, J=14.2 Hz), 6.65(1H, s), 7.02(1H,m), 7.27(1H,m), 7.38(1H, dd, J=15.8 and 8.9 Hz), 7.67(1H, s), 8.24(1H, s), 8.33(2H, d, J=8.6 Hz), 8.43(2H, d, J=8.6 Hz), 9.76(1H, s).

The following compound in example 2 was prepared from (2R,3R)-3-(2,5-difluorophenyl)-3-hydroxy-2-methyl-4-(1H-1,2,4-triazol-1-ly)thiobutyramide in a similar manner to that of Example 1.

EXAMPLE 2

(2R,3R)-2-(2, 5-Difluorophenyl)-3-{3-[4-(1,2,3-thiadiazol-4-yl)phenyl]-1,2,4-thiadiazol-5-yl-}1-(1H-1,2,4-triazol-1-yl)butan-2-ol.

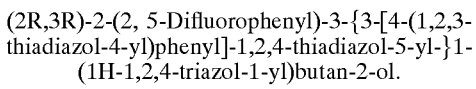

EI-MS: m/z 498 (M$^{30}$); $^1$H-NMR (DMSO d6): δ 1.19(3H, d, J=6.7 Hz), 4.35(1H, q, J=7.1 Hz), 4.55(1H, d, J=14.5 Hz), 4.81(1H, d, J=14.5 Hz), 6.72(1H, s), 7.08~7.15(1H,m), 7.18~7.35(2H, m), 7.68(1H, s), 8.25(1H,s), 8.34(2H, d,J=8.3 Hz), 8.44(2H, d, J=8.3 Hz), 9.77(1H, s).

EXAMPLE 3

(2R,3R)-2-(2,4-Difluorophenyl)-3-{4-[4-(1,2,3-thiadiazol-4-yl)phenyl]thiazol-2-yl}-1-(1H-1,2,4-triazol-1-yl)butan-2-ol.

A mixture of (2R,3R)-3-(2,4-difluorophenyl)-3-hydroxy-2-methyl-4-(1H-1,2,4-triazol-1-yl)thiobutyramide (19.7 mg) and 2-bromo-1-[4-(1,2,3-thiadiazol-4-yl)phenyl]ethanone (27.4 mg) in acetonitrile (3.0 ml) was stirred at room temperature for 1.0 hour. The solution was diluted with ethyl acetate (10 ml), washed with saturated sodium hydrogen carbonate solution (5 ml) and brine (5 ml), dried over anhydrous sodium sulfate, then concentrated in vacuo. The mixture was purified by silica gel column chromatography developed by hexane-ethyl acetate (1:1) to give (2R,3R)-2-(2,4-difluorophenyl)-3-{4-[4-(1,2,3-thiadiazol-4-yl)phenyl]thiazol-2-yl}-1-(1H-1,2,4-triazol-1-yl)butan-2-ol as a pale yellow solid (14.1mg). EI-MS: m/z 497 (M$^+$); $^1$H-NMR (CDCl$_3$): δ 1.26(3H, d, J=6.9 Hz), 4.10(1H, q, J=6.9 Hz), 4.31(1H, d, J=14.3 Hz), 4.92(1H, d, J=14.3 Hz), 6.04(1H, s), 6.76~6.87 (2H, m), 7.48~7.58(1H, m), 7.58(1H, s), 7.68(1H, s), 7.92(1H, s), 8.06(2H, d, J=8.4Hz), 8.16(2H, d, J=8.4 Hz), 8.73(1H, s).

The following compound in example 4 was prepared from (2R,3R)-3-(2,5-difluorophenyl)-3-hydroxy-2-methyl-4-(1H-1,2,4-triazol-1-ly)thiobutyramide in a similar manner to Example 3.

EXAMPLE 4

(2R,3R)-2-(2,5-Difluoropbenyl)-3-{4-[4-(1,2,3-thiadiazol-4-yl)phenyl]thiazol-2-yl}-1-(1H-1,2,4-triazol-1-yl)butan-2-ol.

EI-MS: m/z 497 (M$^{30}$); $^1$H-NMR (CDCl$_3$): 8 1.26(3H, d, J=6.9 Hz), 4.12(1H, q J=6.9 Hz), 4.30(1H, d, J=14.3 Hz), 4.93(1H, d, J=14.3 Hz), 6.06(1H, s), 6.78~6.88(2H, m), 7.48~7.57(1H, m), 7.59(1H, s), 7.69(1H, s), 7.92(1H, s) 8.07(2H, d, J=8.2 Hz), 8.17(2H, d, J=8.2 Hz), 8.74(1H, s).

EXAMPLE 5

(2R,3R)-2-(2,4-Difluorophenyl)-3-{4-[4-(thiazol-2-yl)phenyl]thiazol-2-yl}- 1-(1H-1,2,4-triazol-1-yl)butan-2-ol.

A mixture of (2R,3R)-4-{2-[2-(2,4-difluorophenyl)-2-hydroxy-1-methyl-3-(1H-1,2,4-triazol-1-yl)propyl]thiazol-4-yl}thiobenzamide (20.4 mg), chloroacetal (excess) and 1.0 N hydrochloric acid (0.5 ml) in ethanol (2.5 ml) was stirred at 70° C. for 16 hours. The solution was diluted with ethyl acetate (10 ml), washed with saturated sodium hydrogen carbonate solution (5 ml) and brine (5 ml), dried over anhydrous sodium sulfate, then concentrated in vacuo.

The mixture was purified by silica gel column chromatography developed by hexane-ethyl acetate (1:1) to give (2R,3R)-2-(2,4-difluorophenyl)-3-{4-[4-(thiazole-2-yl) phenyl]thiazol-2-yl}-1 -(1H-1,2,4-triazol-1-yl)butan-2-ol as a pale yellow solid (9.7 mg). EI-MS: m/z 496 (M$^{30}$); $^1$H-NMR (CDCl$_3$): δ 1.25(3H, d, J=6.9 Hz), 4.08(1H, q, J=6.9 Hz), 4.29(1H, d, J=14.4 Hz), 4.91(1H, d, J=14.4 Hz), 6.00(1H, s), 6.75~6.86(2H, m), 7.37(1H, d, J=3.1 Hz), 7.47~7.56(1H, m), 7.56(1H, s), 7.67(1H, s), 7.90(1H, d, J=3.1Hz), 7.91(1H, s,), 7.99(2H, d, J=8.4 Hz), 8.07(2H, d, J=8.4 Hz).

The following compounds in examples 6–16 were prepared in a similar manner to Example 5. Instead of chloroacetal the following reagents were used:

bromoacetone in Examples 6 and 10
1-bromo-2-butanone in Examples 7 and 11
3-bromo-1,1,1-trifluoroacetone in Example 8 and 12
ethyl bromopyruvate in Examples 9 and 13
1-bromo-3,3,4,4,4-pentafluoro-2-butanone in Examples 14 and 15 methyl bromoacetate in Example 16.

EXAMPLE 6

(2R,3R)-2-(2,4-Difluorophenyl)-3-{4-[4-(4-methylthiazol-2-yl) phenyl]thiazol-2-yl}-1-(1H-1,2,4-triazol-1-yl)butan-2-ol.

EI-MS: m/z 510 (M$^+$); $^1$H-NMR (CDCl$_3$): δ 1.25(3H, t, J=7.2 Hz), 2.53(3H, s), 4.08(1H, q, J=7.2 Hz), 4.29(1H, d, J=14.3 Hz), 4.91(1H, d, J=14.3 Hz), 6.00(1H, s), 6.77~6.86 (2H, m), 6.91(1H, s), 7.49~7.55(1H, m), 7.55(1H, s), 7.67 (1H 7.91(1H, s), 7.96(2H, d, J=8.6 Hz), 8.03(2H, d, J=8.6 Hz).

EXAMPLE 7

(2R,3R)-2-(2,4-Difluorophenyl)-3-{4-[4-(4-ethylthiazol-2-yl)phenyl]thiazol-2-yl}-1-(1H-1,2,4-triazol-1-yl)butan-2-ol.

EI-MS: m/z 524 (M$^{30}$); $^1$H-NMR (CDCl$_3$): δ 1.24(3H, d, J=6.9 Hz), 1.37(3H, t, J=7.6Hz), 2.90(2H, q, J=7.6Hz), 4.08(1H, q, J=6.9 Hz), 4.29(1H, d, J=14.4Hz), 4.91(1H, d, J=14.4 Hz), 6.02(1H, s), 6.77~6.86(2H, m), 6.92(1H, s), 7.47~7.56(1H, m), 7.54(1H, s), 7.67(1H, s), 7.91(1H, s), 7.96(2H, d, J=8.7 Hz), 8.04(2H, d, J=8.7 Hz).

EXAMPLE 8

(2R,3R)-2-(2,4-Difluorophenyl)-1-(1H-1,2,4-triazole-1-yl)-3-{4-[4-(4-trifluoromethyl-thiazol-2-yl)phenyl]thiazol-2-yl}butan-2-ol.

EI-MS: m/z 564 (M$^{30}$); $^1$H-NMR (CDCl$_3$): δ 1.25(3H, t, J=7.1 Hz), 4.09(1H, q, J=7.1 Hz), 4.12(1H, d, J=7.1 Hz), 4.29(1H, d, J=7.1 Hz), 5.94(1H, s), 6.78~6.86(2H, m), 7.47~7.57(1H, m), 7.60(1H, s), 7.68(1H, s), 7.77(1H, s 7.89(1H, s), 8.01(2H, d, J=8.4 Hz), 8.08(2H, d, J=8.4 Hz).

EXAMPLE 9

2-(4-{2-[(1R,2R)-2-(2,4-Difluorophenyl)-2-hydroxy-1-methyl-3-(1H-1,2,4-triazol-1-yl)propyl]thiazol-4-yl}phenyl)thiazole-4-carboxylic acid ethyl ester.

EI-MS: m/z 568 (M$^{30}$); $^1$H-NMR (CDCl$_3$): δ 1.25(3H, d, J=7.2 Hz), 1.45(3H, t, J=7.1Hz), 4.09(1H, q, J=7.2Hz), 4.29(1H, d, J=14.2Hz), 4.47(2H, q, J=7.1 Hz), 4.92(1H, d, J=14.2 Hz), 5.95(1H, s), 6.77~6.86(2H, m), 7.47~7.56(1H, m), 7.58(1H, s), 7.67(1H, s), 7.90(1H, s), 8.00(2H, d, J=8.2 Hz), 8.11(2H, d, J=8.2 Hz), 8.19(1H, s).

EXAMPLE 10

(2R,3R)-2-(2,4-Difluorophenyl)-3-{3-[4-(4-methylthiazol-2-yl)phenyl]-1,2,4-thiadiazol-5-yl}-1-(1H-1,2,4-triazol-1-yl)butan-2-ol.

EI-MS: m/z 511(Mt); $^1$H-NMR (CDCl$_3$): δ 1.23(3H, d, J=7.3 Hz), 2.54(3H, s), 4.26(1H, q, J=7.3 Hz), 4.30(1H, d,

J=14.5 Hz), 4.95(1H, d, J=14.5 Hz), 5.70(1H,br), 6.77~6.86 (2H, m), 6.94(1H, s), 7.48~7.54(1H, m), 7.77(1H, s), 7.81 (1H, s), 8.07(2H, d, J=8.6 Hz), 8.38(2H, d, J=8.6 Hz).

EXAMPLE 11

(2R,3R)-2-(2,4-Difluorophenyl)-3-{3-[4-(4-ethylthiazol-2-yl)phenyl]-1,2,4-thiadiazol-5-yl}-1-(1H-1,2,4-triazol-1-yl)butan-2-ol.

EI-MS: m/z 525 ($M^{30}$); $^1$H-NMR (CDCl$_3$): δ 1.23(3H, d, J=6.9 Hz), 1.37(3H, t, J=7.6Hz), 2.90(2H, q, J=7.6Hz), 4.26(1H, q, J=6.9Hz), 4.30(1H, d, J=14.2Hz), 4.95(1H, d, J=14.2 Hz), 5.70(1H, br), 6.79~6.87(2H, m), 6.95(1H, s), 7.45~7.52(1H, m), 7.77(1H, s), 7.81(1H, s), 8.08(2H, d, J=8.2Hz), 8.38(2H, d, J=8.2 Hz).

EXAMPLE 12

(2R,3R)-2-(2,4-Difluorophenyl)-1-(1H-1,2,4-triazol-1-yl)-3-{3-[4-(4-trifluoromethylthiazol-2-yl)phenyl]-1,2,4-thiadiazol-5-yl}butan-2-ol.

EI-MS: m/z 569($M^{30}$); $^1$H-NMR (CDCl$_3$): δ 1.24(3H, d, J=7.3 Hz), 4.27(1H, q, J=7.3 Hz), 4.30 (1H, d, J=15.0 Hz), 4.95(1H, d, J=15.0 Hz), 5.69(1H, s), 6.79~6.87(2H, m), 7.48~7.55(1H, m), 7.77(1H, s), 7.80(2H, s), 8.12(2H, d, J=8.6 Hz), 8.43(2H, d, J=8.6 Hz).

EXAMPLE 13

2-(4-{5-[(1R, 2R)-2-(2,4-Difluorophenyl)-2-hydroxy-1-methyl-3-(1H-1,2,4-triazol-1-yl)propyl]-1,2,4-thiadiazol-3-yl}phenyl)thiazole-4-carboxylic acid ethyl ester.

EI-MS: m/z 569 ($M^{30}$); $^1$H-NMR (CDCl$_3$): δ 1.24(3H, d, J=7.3 Hz), 1.45(3H, t, J=7.3Hz), 4.27 (1H, q, J=7.3Hz),4.30 (1H, d, J=14.2Hz), 4.47(2H, q, J=7.3Hz), 4.95(1H, d, J=14.2 Hz), 5.69(1H, s), 6.78~6.87(2H, m), 7.46~7.55(1H, m), 7.79(2H, d, J=8.6 Hz), 8.14(1H, s), 8.17(1H, s), 8.21(1H, s), 8.42(2H, d, J=8.6 Hz).

EXAMPLE 14

(2R,3R)-2-(2,4-Difluorophenyl)-3-{4-[4-(4-pentafluoroethylthiazol-2-yl)phenyl]thiazol-2-yl}-1-(1H-1,2,4-triazol-1-yl)butan-2-ol.

EI-MS: m/z 614 ($M^{30}$); $^1$H-NMR(CDCl$_3$): δ 1.25(3H, t, J=7.2 Hz), 4.09(1H, q, J=7.2 Hz), 4.30(1H, d, J=14.4 Hz), 4.92(1H, d, J=14.4 Hz), 5.95(1H, s), 6.76~6.86(2H, m), 7.47~7.57(1H, m), 7.59(1H, s), 7.68(1H, s), 7.82(1H, s 7.90(1H, s), 8.00(2H, d, J=8.4 Hz), 8.07(2H, d, J=8.4 Hz).

EXAMPLE 15

(2R,3R)-2-(2,4-Difluorophenyl)-3-{3-[4-(4-pentafluoroethylthiazol-2-yl) phenyl]-1,2,4-thiadiazol-5-yl}-1-(1H-1,2,4-triazol-1-yl)butan-2-ol.

EI-MS: m/z 615 ($M^{30}$); $^1$H-NMR (CDCl$_3$): δ 1.24(3H, d, J=7.3 Hz), 4.26~4.34(1H, m), 4.31(1H, d, J=14.2 Hz), 4.95(1H, d, J=14.2 Hz), 5.69(1H,s), 6.79~6.87(2H, m), 7.48~7.55(1H, m), 7.77(1H, s), 7.80(1H, s), 7.84(1H, s), 8.12(2H, d, J=8.6 Hz), 8.43(2H, d, J=8.6 Hz).

EXAMPLE 16

(2R,3R)-2-(2,4-Difluorophenyl)-3-{4-[4-(4-hydroxythiazol-2-yl) phenyl]thiazol-2-yl}-1-(1H-1,2,4-triazol-1-yl)butan-2-ol.

EI-MS: m/z 512 ($M^{30}$); $^1$H-NMR (CDCl$_3$): δ 1.25(3H, d, J=6.9 Hz), 4.12(1H, q, J=6.9 Hz), 4.28(1H ,d, J=14.0 Hz), 4.93(1H, d, J=14.0 Hz), 5.79(1H, s), 6.78~6.86(2H, m), 7.47~7.56(1H, m), 7.69(1H, s), 7.70(1H, s), 7.87(1H, s), 7.89~7.98(1H, m), 8.08(2H, d, J=8.4 Hz), 8.24(2H, d, J=8.4 Hz).

EXAMPLE 17

(2R,3R)-2-(2,4-Difluorophenyl)-3-(3-{4-[5-methyl-(1,2,4-thiadiazol-3-yl)]phenyl}-1,2,4-thiadiazol-5-yl)-1-(1H-1,2,4-triazol-1-yl)butan-2-ol.

To a mixture of (2R,3R)-4-{5-[2-(2,4-difluorophenyl)-2-hydroxy-1-methyl-3-(1H-1,2,4-triazol-1-yl)propyl]-1,2,4-thiadiazol-3-yllthiobenzamide (20.0 mg) and thioacetamide (20.2 mg) in ethanol (3.0 ml) was added iodine (95.8 mg) at room temperature. The solution was stirred for 60 hours and diluted with ethyl acetate (10 ml), washed with sodium thiosulfate solution (5 ml) and brine (5 ml), dried over anhydrous sodium sulfate, then concentrated in vacuo. The mixture was purified by silica gel column chromatography developed by hexane-ethyl acetate (1:1) to give (2R,3R)-2-(2,4-difluorophenyl)-3-(3-{4-[5-methyl-(1,2,4-thiadiazol-3-yl)]phenyl}-1,2,4-thiadiazol-5-yl)-1-(1H-1,2,4-triazol-1-yl) butan-2-ol as a pale yellow solid (7.5 mg). EI-MS: m/z 512 ($M^{30}$); $^1$H-NMR (CDCl$_3$): δ 1.24(3H, d, J=7.3 Hz), 2.76(3H, s), 4.26 (1H, q, J=7.3 Hz), 4.30(1H, d, J=14.4 Hz), 4.95(1H, d, J=14.4 Hz), 5.69(1H, s), 6.78~6.87(2H, m), 7.45~7.54 (1H, m), 7.77(1H, s), 7.80(1H, s), 8.08(2H, d, J=8.6 Hz), 8.45(2H, d, J=8.6 Hz).

The following compounds in examples 18–20 were prepared in a similar manner to Example 17.

EXAMPLE 18

(2R,3R)-2-(2,4-Difluorophenyl)-3-(4-{4-[5-methyl-(1,2,4-thiadiazol-3-yl)]phenyl}thiazol-2-yl)-1-(1H-1,2,4-triazol-1-yl)butan-2-ol.

EI-MS: m/z 511($M^{30}$); $^1$H-NMR (CDCl$_3$): δ 1.25(3H, d, J=7.2 Hz), 2.76(3H, s), 4.12(1H, q, J=7.2 Hz), 4.29(1H, d, J=14.5 Hz), 4.92(1H, d, J=14.5 Hz), 5.89(1H, s), 6.77~6.83 (2H, m), 7.47~7.58(1H, m), 7.62(1H, s), 7.68(1H, s), 7.89 (1H, s, 8.04(4H, s).

EXAMPLE 19

(2R,3R)-2-(2,4-Difluorophenyl)-3-{4-[5-ethyl-(1,2,4-thiadiazol-3-yl)]phenyl}thiazol-2-yl)-1-(1H-1,2,4-triazol-1-yl)butan-2-ol.

EI-MS: m/z 525 ($M^{30}$); $^1$H-NMR (CDCl$_3$): δ 1.25(3H, d, J=7.2 Hz), 1.47(3H, t, J=7.6 Hz), 3.10(2H, q, J=7.6 Hz), 4.10(1H, q, J=7.2 Hz), 4.29(1H, d, J=14.2 Hz), 4.92(1H, d, J=14.2 Hz), 5.91(1H, s), 6.77~6.86(2H, m), 7.47~7.57(1H, m), 7.62(1H, s), 7.68(1H, s), 7.89(1H, s), 8.04(4H, s).

EXAMPLE 20

(2R,3R)-2-(2,4-Difluorophenyl)-3-(3-{4-[5-ethyl-(1,2,4-thiadiazol-3-yl)]phenyl}-1,2,4-thiadiazol-5-yl)-1-(1H-1,2,4-triazol-1-yl)butan-2-ol.

EI-MS: m/z 526($M^{30}$); $^1$H-NMR (CDCl$_3$): δ 1.24(3H, d, J=7.3 Hz), 1.47(3H, t, J=7.6 Hz), 3.10(2H, q, J=7.6 Hz), 4.25~4.31(1H, m), 4.31(1H, d, J=14.2 Hz), 4.94(1H, d, J=14.2 Hz), 5.69(1H, s), 6.78~6.83(2H, m), 7.47~7.55(1H, m), 7.78(1H, s), 7.80(1H, s), 8.09(2H, d, J=7.9 Hz), 8.45 (2H, d, J=7.9 Hz).

EXAMPLE A

Hard gelatine capsules each containing the following ingredients were manufactured in conventional manner:

| | |
|---|---|
| Compound of Example 1 | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

EXAMPLE B

Tablets each containing the following ingredients were manufactured in conventional manner:

| | |
|---|---|
| Compound of Example 1 | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

What is claimed is:

1. A compound of the formula,

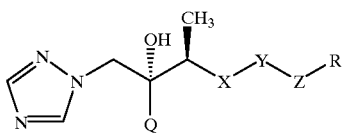
(I)

wherein
Q is a phenyl ring which is unsubstituted or substituted by 1 to 3 halogen atom(s);
R is hydrogen, hydroxy, carboxy, carbamoyl, cyano, lower-alkyl, lower-alkoxycarbonyl or lower-alkoxy, wherein said lower-alkyl, lower-alkoxycarbonyl and lower-alkoxy is unsubstitued or substituted by one or more halogen, lower-alkyl, di-lower-alkylamino or lower-alkoxy;
X is a 5 or 6 membered hetero-aromatic ring;
Y is phenyl or pyridyl, each of which is unsubstitued or substituted by one or more halogen, cyano, lower-alkyl, di-lower-alkylamino, lower-alkyloxy, acyl, lower-alkoxycarbonyl; and
Z is a sulfur and nitrogen containing 5 membered hetero-aromatic ring; or pharmaceutically acceptable salts thereof.

2. The compound according to claim 1, wherein Q is a radical selected from the group consisting of 2-fluorophenyl, 4-fluorophenyl, 2-chlorophenyl, 4-chlorophenyl, 2-bromophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, and 4-bromo-2,5-difluorophenyl.

3. The compound according to claim 1, wherein Q is a radical selected from the group consisting of 2-fluorophenyl, 4-fluorophenyl, 2,4-difluorophenyl, 2,5-difluorophenyl, 2,4,6-trifluorophenyl, 4-bromo-2,5-difluorophenyl.

4. The compound according to claim 1, wherein X is a radical selected from the group consisting of:

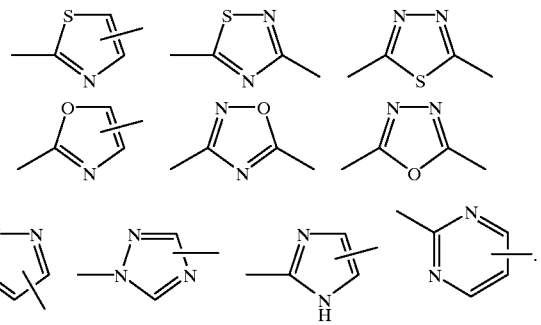

5. The compound according to claim 4, wherein X is the radical

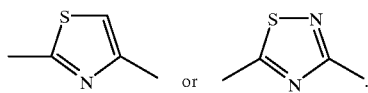

6. The compound according to claim 1, wherein Y is a radical selected from the group consisting of o-phenylene, m-phenylene, p-phenylene, pyridin-2,4-diyl, pyridin-2,5-diyl and pyridin-2,6-diyl.

7. The compound according to claim 6, wherein Y is a radical selected from the group consisting of m-phenylene, p-phenylene, and pyridin-2,5-diyl.

8. The compound according to claim 1, wherein Z is a radical selected from the group consisting of:

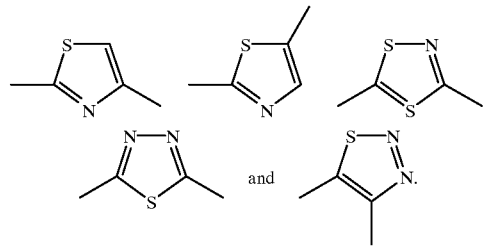

9. The compound according to claim 8 wherein Z is the radical

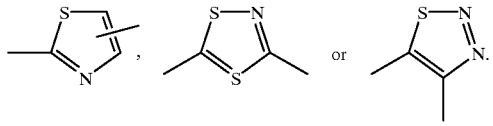

10. The compound according to claim 9 wherein Z is the radical

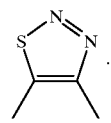

11. The compound according to claim 1, wherein R is a radical selected from the group consisting of hydrogen, hydroxy, lower-alkyl, lower-alkoxycarbonyl and lower-alkyl substituted by one or more halogen.

12. The compound according to claim 1, wherein —Z—R is a radical selected from the group consisting of thiazole-2-yl, 4-methyl-thiazol-2-yl, 4-isopropyl-thiazol-2-yl, 4-ethyl-thiazol-2-yl, 4-trifluoromethyl-thiazol-2-yl, 4-pentafluoroethyl-thiazol-2-yl, 4-acetyl-thiazol-2-yl, 4-carboxy-thiazol-2-yl, 4-cyano-thiazol-2-yl, 4-methoxy-thiazol-2-yl, 4-ethoxycarbonyl-thiazol-2-yl, 4-chloro-thiazol-2-yl, 4-hydroxy-thiazol-2-yl, 1,2,4-thiadiazol-3-yl, 5-methyl-1,2,4-thiadiazol-3-yl, 5-ethyl-1,2,4-thiadiazol-3-yl, 5-isopropyl-1,2,4-thiadiazol-3-yl, 5-trifluoromethyl-1,2,4-thiadiazol-3-yl, 5-pentafluoroethyl-1,2,4-thiadiazol-3-yl, 5-acetyl-1,2,4-thiadiazol-3-yl, 5-carboxy-1,2,4-thiadiazol-3-yl, 5-cyano-1,2,4-thiadiazol-3-yl, 5-methoxy-1,2,4-thiadiazol-3-yl, 5-ethoxycarbonyl-1,2,4-thiadiazol-3-yl, 5-chloro-1,2,4-thiadiazol-3-yl, 1,3,4-thiadiazol-5-yl, 2-methyl-1,3,4-thiadiazol-5-yl, 2-ethyl-1,3,4-thiadiazol-5-yl, 2-isopropyl-1,3,4-thiadiazol-5-yl, 2-trifluoromethyl-1,3,4-thiadiazol-5-yl, 2-pentafluoroethyl-1,3,4-thiadiazol-5-yl, 2-acetyl-1,3,4-thiadiazol-5-yl, 2-carboxy-1,3,4-thiadiazol-5-yl, 2-cyano-1,3,4-thiadiazol-5-yl, 2-methoxy-1,3,4-thiadiazol-5-yl, 2-ethoxycarbonyl-1,3,4-thiadiazol-5-yl, 2-chloro-1,3,4-thiadiazol-5-yl, 1,2,3-thiadiazol-4-yl, 5-methyl-1,2,3-thiadiazol-4-yl, 5-ethyl-1,2,3-thiadiazol-4-yl, 5-isopropyl-1,2,3-thiadiazol-4-yl, 5-trifluoromethyl-1,2,3-thiadiazol-4-yl, 5-penta-fluoroethyl-1,2,3-thiadiazol-4-yl, 5-acetyl-1,2,3-thiadiazol-4-yl, 5-carboxy-1,2,3-thiadiazol-4-yl, 5-cyano-1,2,3-thiadiazol-4-yl, 5-methoxy-1,2,3-thiadiazol-4-yl, 5-ethoxycarbonyl-1,2,3-thiadiazol-4-yl and 5-chloro-1,2,3-thiadiazol-4-yl.

13. The compound according to claim 1, wherein —Z—R is a radical selected from the group consisting of thiazole-2-yl, 4-methyl-thiazol-2-yl, 4-ethyl-thiazol-2-yl, 4-trifluoromethyl-thiazol-2-yl, 4-pentafluoroethyl-thiazol-2-yl, 4-ethoxycarbonyl-thiazol-2-yl, 4-chloro-thiazol-2-yl, 4-hydroxy-thiazol-2-yl, 1,2,4-thiadiazol-3-yl, 5-methyl-1,2,4-thiadiazol-3-yl and 5-ethyl-1,2,4-thiadiazol-3-yl.

14. The compound according to claim 1, which is selected from the group consisting of:

(2R,3R)-2-(2,4-difluorophenyl)-3-{3-[4-(1,2,3-thiadiazol-4-yl)phenyl]-1,2,4-thiadiazol-5-yl}-1-(1H-1,2,4-triazol-1-yl)butan-2-ol, (2R,3R)-2-(2,5-difluorophenyl)-3-{3-[4-(1,2,3-thiadiazol-4-yl) phenyl]-1,2,4-thiadiazol-5-yl}-1-(1H-1,2,4-triazol-1-yl)butan-2-ol, (2R,3R)-2-(2,4-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,5-difluorophenyl)-3-{4-[4-(1,2,3-thiadiazol-4-yl)phenyl]thiazol-2-yl}-1-(1H-1,2,4-triazol-1-yl)butan-2-ol, (2R,3R)-2-(2,4-difluorophenyl)-3-t4-[4-(thiazol-2-yl) phenyl]thiazol-2-yl}-1-(1H-1,2,4-triazol-1-yl)butan-2-ol, (2R,3R)-2-(2,4-difluorophenyl)-3-{4-[4-(4-methylthiazol-2-yl)phenyl]thiazol-2-yl}-1-(1H-1,2,4-triazol-1-yl)butan-2-ol, (2R,3R)-2-(2,4-difluorophenyl)-3-{4-[4-(4-ethylthiazol-2-yl)phenyl]thiazol-2-yl}-1-(1H-1,2,4-triazol-1-yl)butan-2-ol, (2R,3R)-2-(2,4-difluorophenyl)-1-(1H-1,2,4-triazole-1-yl)-3-{4-[4-(4-trifluoromethylthiazol-2-yl)phenyl]thiazol-2-yl}butan-2-ol, 2-(4-{2-[(1R,2R)-2-(2,4-difluorophenyl)-2-hydroxy-1-methyl-3-(1H-1,2,4-triazol-1-yl)propyl]thiazol-4-yl}phenyl)thiazole-4-carboxylic acid ethyl ester, (2R,3R)-2-(2,4-difluorophenyl)-3- 3-[4-(4-methylthiazol-2-yl) phenyl]-1,2,4-thiadiazol-5-yl}-1-(1H-1,2,4-triazol-1-yl)butan-2-ol, (2R,3R)-2-(2,4-difluorophenyl)-3- {3-[4-(4-ethylthiazol-2-yl)phenyl ]-1,2,4-thiadiazol-5-yl}-1-(1H-1,2,4-triazol-1-yl)butan-2-ol, (2R,3R)-2-(2,4-difluorophenyl)-1-(1H-1,2,4-triazol-1-yl)-3-{3-[4-(4-trifluoromethylthiazol-2-yl)phenyl]-1,2,4-thiadiazol-5-yl}butan-2-ol, 2-(4-{5-[(1R,2R)-2-(2,4-difluorophenyl)-2-hydroxy-1-methyl-3-(1H-1,2,4-triazol-1-yl)propyl]-1,2,4-thiadiazol-3-yl}phenyl)thiazole-4-carboxylic acid ethyl ester, (2R,3R)-2-(2,4-difluorophenyl)-3-{4-[4-(4-pentafluoroethylthiazol-2-yl)phenyl]thiazol-2-yl}1-(1H-1,2,4-triazol-1-yl)butan-2-ol, (2R,3R)-2-(2,4-difluorophenyl)-3-{3-[4-(4-pentafluoroethylthiazol-2-yl)phenyl]-1,2,4-thiadiazol-5-yl}-1-(1H-1,2,4-triazol-1-yl)butan-2-ol, (2R,3R)-2-(2,4-difluorophenyl)-3-{4-[4-(4-hydroxythiazol-2-yl)phenyl]thiazol-2-yl}-1-(1H-1,2,4-triazol-1-yl)butan-2-ol, (2R,3R)-2-(2,4-difluorophenyl)-3-(3-{4-[5-methyl-(1,2,4-thiadiazol-3-yl)]phenyl}-1,2,4-thiadiazol-5-yl)-1-(1H-1,2,4-triazol-1-yl)butan-2-ol, (2R,3R)-2-(2,4-difluorophenyl)-3-(4-{4-[5-methyl-(1,2,4-thiadiazol-3-yl)]phenyl}thiazol-2-yl)-1-(1H-1,2,4-triazol-1-yl)butan-2-ol, (2R,3R)-2-(2,4-difluorophenyl)-3-(4-{4-[5-ethyl-(1,2,4-thiadiazol-3-yl)]phenyl}thiazol-2-yl)-1-(1H-1,2,4-triazol-1-yl)butan-2-ol, and (2R,3R)-2-(2,4-difluorophenyl)-3-(3-{14-[5-ethyl-(1,2,4-thiaziazol-3-yl)]phenyl}-1,2,4-thiadiazol-5-yl)-1-(1H-1,2,4-triazol-1-yl)butan-2-ol.

15. A pharmaceutical composition comprising a pharmaceutically effective amount of a compound according to claim 1 as an active ingredient and one or more pharmaceutically acceptable carrier(s).

\* \* \* \* \*